United States Patent
Muhanna et al.

(10) Patent No.: US 8,628,575 B2
(45) Date of Patent: Jan. 14, 2014

(54) VERTEBRAL BODY REPLACEMENT AND METHOD OF USE

(75) Inventors: Nabil L. Muhanna, Gainesville, GA (US); David L. Schalliol, Oakwood, GA (US)

(73) Assignee: Nabil L. Muhanna, Gainesville, GA (US)

(*) Notice: Subject to any disclaimer, the term of this patent is extended or adjusted under 35 U.S.C. 154(b) by 0 days.

(21) Appl. No.: 13/245,012

(22) Filed: Sep. 26, 2011

(65) Prior Publication Data

US 2012/0046751 A1 Feb. 23, 2012

Related U.S. Application Data

(63) Continuation of application No. 10/701,883, filed on Nov. 5, 2003, now abandoned, which is a continuation-in-part of application No. 09/941,040, filed on Aug. 28, 2001, now abandoned, said application No. 10/701,883 is a continuation-in-part of application No. 09/947,851, filed on Sep. 6, 2001, now Pat. No. 6,824,565.

(60) Provisional application No. 60/228,694, filed on Aug. 29, 2000, provisional application No. 60/231,142, filed on Sep. 8, 2000, provisional application No. 60/476,075, filed on Jun. 5, 2003.

(51) Int. Cl.
*A61F 2/44* (2006.01)

(52) U.S. Cl.
USPC .................. 623/17.11; 623/16.11; 623/11.11

(58) Field of Classification Search
USPC .................. 623/17.11–18.11, 11.11, 16.11
See application file for complete search history.

(56) References Cited

U.S. PATENT DOCUMENTS

| | | |
|---|---|---|
| 3,875,595 A | 4/1975 | Froning |
| 4,349,921 A | 9/1982 | Kuntz |

(Continued)

FOREIGN PATENT DOCUMENTS

| | | |
|---|---|---|
| WO | WO 97-25945 | 7/1997 |
| WO | WO 99-11203 | 3/1999 |

OTHER PUBLICATIONS

Experience and Short-Term Results with No-React Cardiovascular Implants—Chapter 15—Advances in Anticalcific and Antidegenerative Treatment of Heart Valve Bioprostheses, First Edition, S. Milo, Y Bar-El, V. Kertsman, S. Sawaed, A. Hoffman, Silent Partners, Inc., Austin, 1997.

(Continued)

*Primary Examiner* — Thomas J Sweet
*Assistant Examiner* — Christopher D Prone
(74) *Attorney, Agent, or Firm* — Womble Carlyle Sandridge & Rice LLP

(57) ABSTRACT

Vertebral body replacements are provided, including at least one vertebral body replacement in the shape of an oblong object. The oblong vertebral body replacement includes a nose shape to provide as minimally invasive an installation as possible, serrations formed in the side wall of the body replacement's body to prevent expulsion once the body replacement is in place, a tapered asymmetric shape to provide spinal lordosis, and an integral protrusion for stability and to increase the bearing area to reduce contact pressure between the body replacement and the vertebral plate. Hollow passages are typically filled with bone tissue. The body is also provided with holes passing therethrough to promote tissue growth.

24 Claims, 15 Drawing Sheets

(56) References Cited

U.S. PATENT DOCUMENTS

| | | |
|---|---|---|
| 4,479,491 A | 10/1984 | Martin |
| 4,599,086 A | 7/1986 | Doty |
| 4,714,469 A | 12/1987 | Kenna |
| 4,834,757 A | 5/1989 | Brantigan |
| 4,863,477 A | 9/1989 | Monson |
| 4,878,915 A | 11/1989 | Brantigan |
| 5,192,327 A | 3/1993 | Brantigan |
| 5,306,309 A | 4/1994 | Wagner |
| 5,314,477 A | 5/1994 | Marnay |
| 5,320,644 A | 6/1994 | Baumgartner |
| 5,397,364 A | 3/1995 | Kozak et al. |
| 5,425,772 A | 6/1995 | Brantigan |
| 5,484,437 A | 1/1996 | Michelson |
| 5,499,984 A | 3/1996 | Steiner et al. |
| 5,549,673 A | 8/1996 | Beale |
| 5,609,635 A | 3/1997 | Michelson |
| 5,609,636 A | 3/1997 | Kohrs et al. |
| 5,674,296 A | 10/1997 | Bryan et al. |
| 5,693,100 A | 12/1997 | Pisharodi |
| 5,722,977 A | 3/1998 | Wilhelmy |
| 5,755,798 A | 5/1998 | Papavero et al. |
| 5,776,196 A | 7/1998 | Matsuzaki et al. |
| 5,776,197 A | 7/1998 | Rabbe et al. |
| 5,782,919 A | 7/1998 | Zdeblick et al. |
| 5,865,848 A | 2/1999 | Baker |
| 5,916,267 A | 6/1999 | Tienboon |
| 5,961,554 A | 10/1999 | Janson et al. |
| 5,989,291 A | 11/1999 | Ralph et al. |
| 6,004,326 A | 12/1999 | Castro et al. |
| 6,030,390 A | 2/2000 | Mehdizadeh |
| 6,033,438 A | 3/2000 | Bianchi et al. |
| 6,056,749 A | 5/2000 | Kuslich |
| 6,059,790 A | 5/2000 | Sand et al. |
| 6,096,080 A | 8/2000 | Nicholson et al. |
| 6,096,081 A | 8/2000 | Grivas et al. |
| 6,102,950 A * | 8/2000 | Vaccaro ............. 623/17.16 |
| 6,111,164 A | 8/2000 | Rainey et al. |
| 6,120,506 A | 9/2000 | Kohrs et al. |
| 6,140,452 A | 10/2000 | Felt et al. |
| 6,143,033 A | 11/2000 | Paul et al. |
| 6,146,422 A | 11/2000 | Lawson |
| 6,224,607 B1 | 5/2001 | Michelson |
| 6,270,528 B1 | 8/2001 | McKay |
| 6,277,149 B1 | 8/2001 | Boyle et al. |
| 6,283,966 B1 | 9/2001 | Houfburg |
| 6,322,588 B1 | 11/2001 | Ogle et al. |
| 6,368,325 B1 | 4/2002 | McKinley et al. |
| 6,395,032 B1 | 5/2002 | Gauchet |
| 6,520,967 B1 | 2/2003 | Cauthen |
| 6,682,562 B2 | 1/2004 | Viart et al. |
| 6,821,298 B1 * | 11/2004 | Jackson ............. 623/17.15 |
| 6,824,565 B2 | 11/2004 | Muhanna et al. |
| 6,890,355 B2 | 5/2005 | Michelson |
| 2001/0039458 A1 | 11/2001 | Boyer, II et al. |
| 2002/0029082 A1 | 3/2002 | Muhanna |
| 2002/0045944 A1 | 4/2002 | Muhanna et al. |

OTHER PUBLICATIONS

No-React Detoxification Process: A Superior Anticalcification Method for Bioprostheses Abolhoda, M.D. et al.—1996—The Society of Thoracic Surgeons—Published by Elsevier Science, Inc.—pp. 1724-1730.

Calcification of Bovine Pericardium: Glutaraldehyde Versus No-React Biomodiciation—Abolhoda, M.D. et al.—1996—The Society of Thoracic Surgeons—Published by Elsevier—pp. 169-174.

Construction Factors Influencing the Shelhigh Porcine Bioprosthesis—Chapter 18—Advances in Anticalcific and Antidenerative—Treatment of Heart Valve Bioprostheses, First Edition, edited by Shlomo Gabbay, M.D., David J. Wheatley, M.D., Silent Partners, Inc., Austin, 1997.

Review—The Artificial Disc: Theory, Design and Materials—Qi-Bin Bao et al.—Biomaterials 1998—pp. 1157-1167.

Shelhigh No React Patch—p. 1 of 1—Dec. 6, 2000—http://www.cosmo-tec.com/products/cs/shellhigh/e-shelhigh.htm.

Tsantrizos et al., *A Comparative Biomechanical Study of Posterior Lumbar Interbody Fusion Implants*, 1997 Masters Thesis, Orthopaedic Research Laboratory, Division of Orthopaedic Surgery McGill University, Montreal, Qc, Canada, The Uniformed Services, University of the Health Sciences, Bethesda, Maryland, U.S.A.

Medical Multimedia Group, *A Patient's Guide to Low Back Pain*, www.sechrest.com/mmg/back/backpain.html, pp. 1-15, Jul. 14, 2000.

Northwest Spine Surgery, *BAK Interbody Fusion. . .* , www.backsurgery.com/bak1.htm, pp. 1-2 © 1998.

J. Flood—*Titanium cage lumbar interbody fusion*, © 1997, 1998—http://www.irmc.org/about/ortho/ga_titanium.html, May 22, 2000.

Sulzer Spine-Tech—The BAK™ Patient Information, *An Innovative Approach to Surgical Spinal Treatment*, http://www.spine-tech.com/BAK-IPSIndex.html, May 22, 2000.

Sulzer Spine-Tech—The BAK™ Patient Information, *About BAK*, pp. 1-2, http://www.spine-tech.com/BAK-IPSBAKTechnology.html, May 22, 2000.

Sulzer Spine-Tech-The BAK™ Patient Information, *How BAK Works*, http://www.spine-tech.com/BAK-IFSHowBAKWorks.html, May 22, 2000.

Sulzer Spine-Tech—The BAK™ Patient Information, *Clinical Results, Prospective Multi-Center Clinical Trial of the BAK™ Fusion System*, pp. 1-18, http://www.spine-tech.com/BAK-IFSClinicalResults.html, May 22, 2000.

Workshop on No-React Bioprostheses, Brussels Hilton Hotel, Sep. 23, 1998, 12$^{th}$ EACTS Annual Meeting, Moderator: Dr. Shlomo Gabbay.

\* cited by examiner

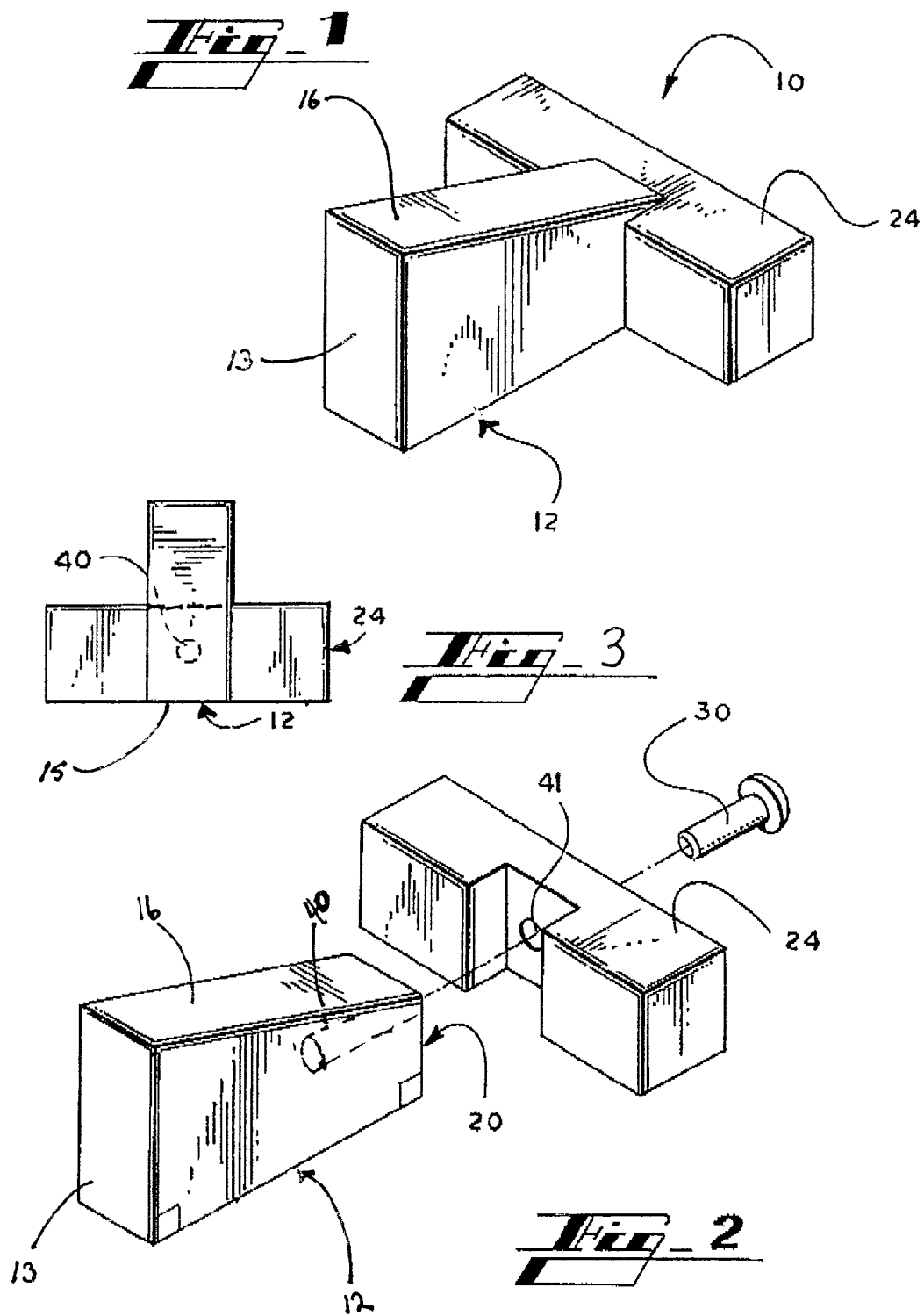

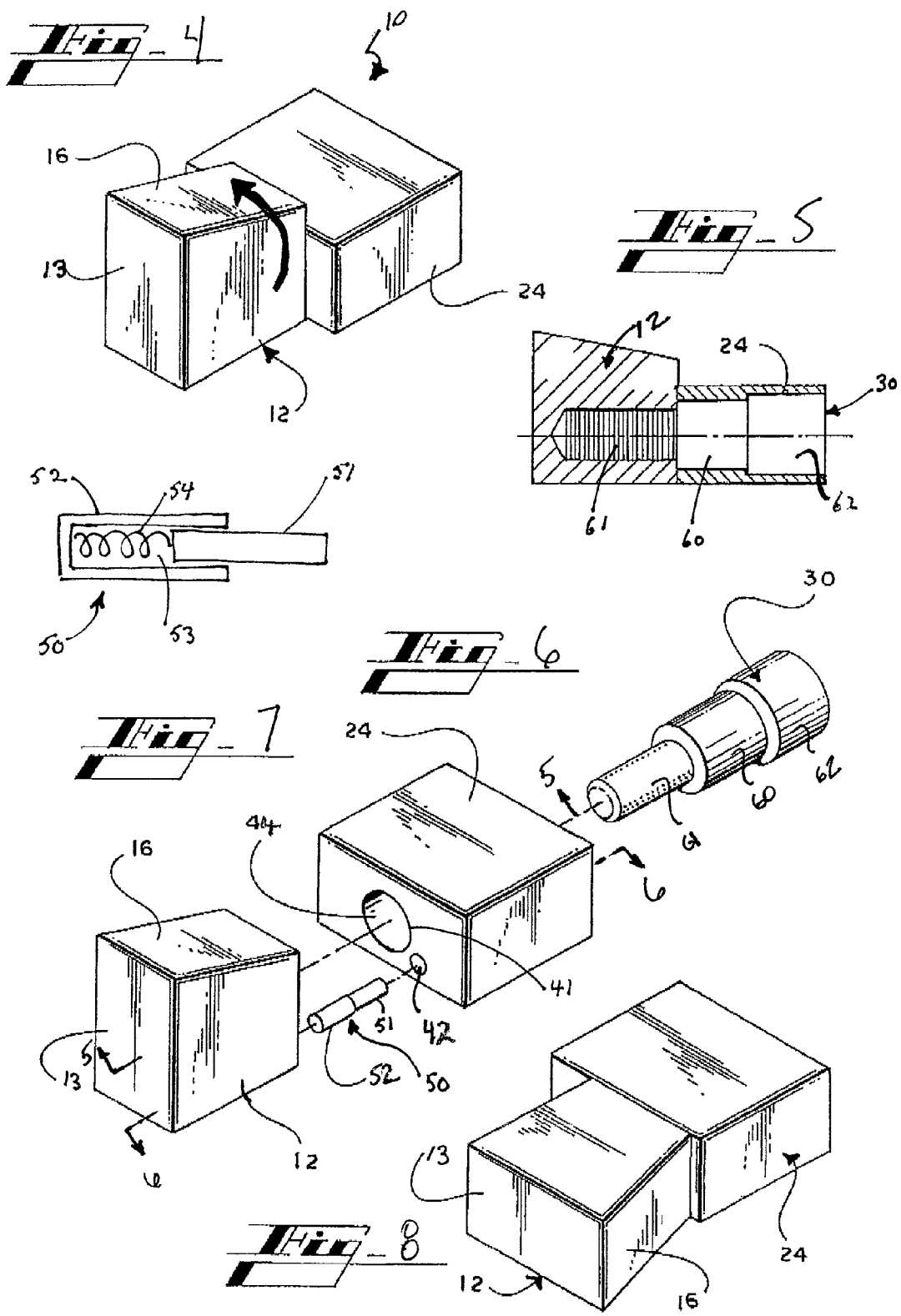

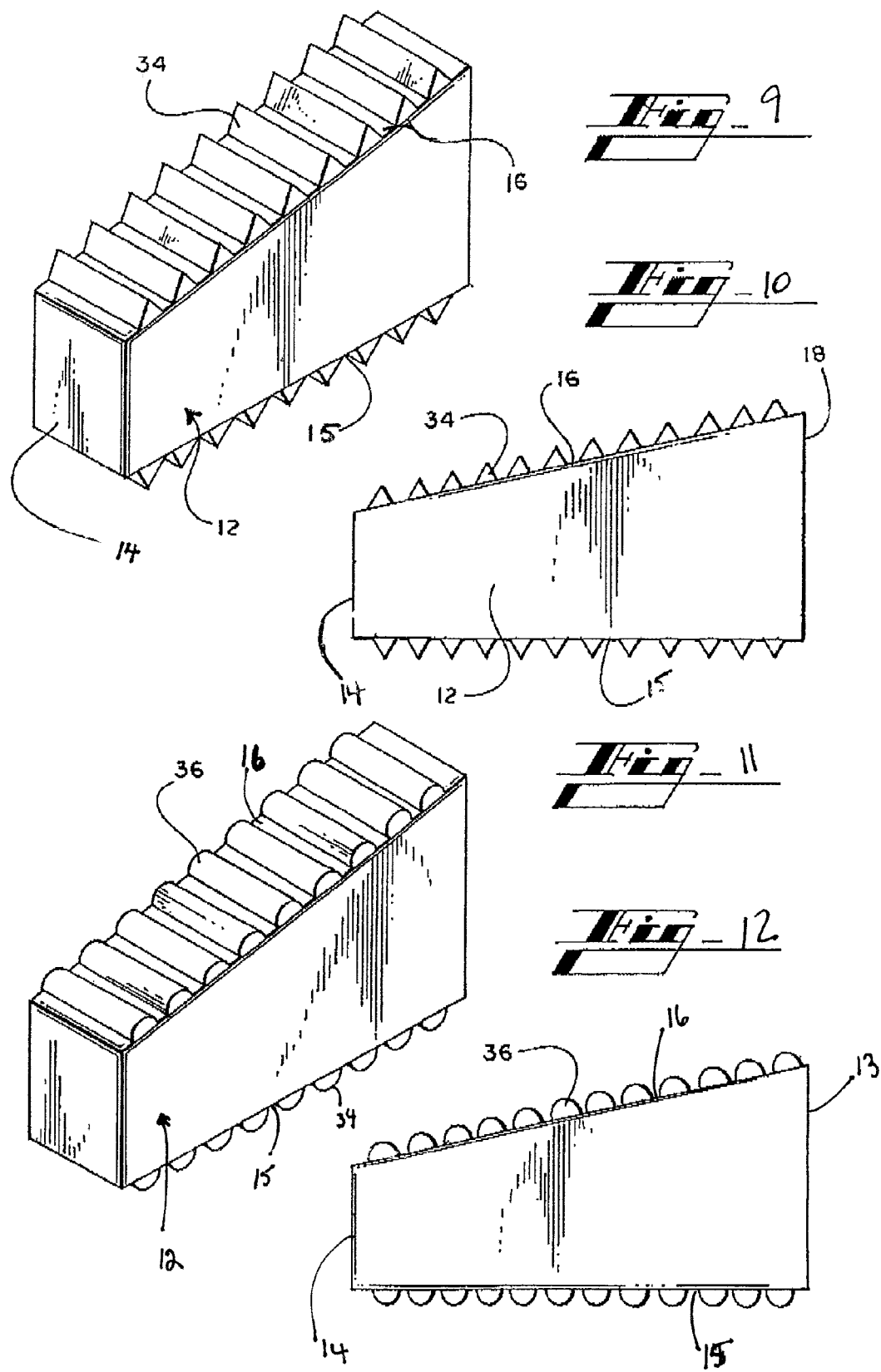

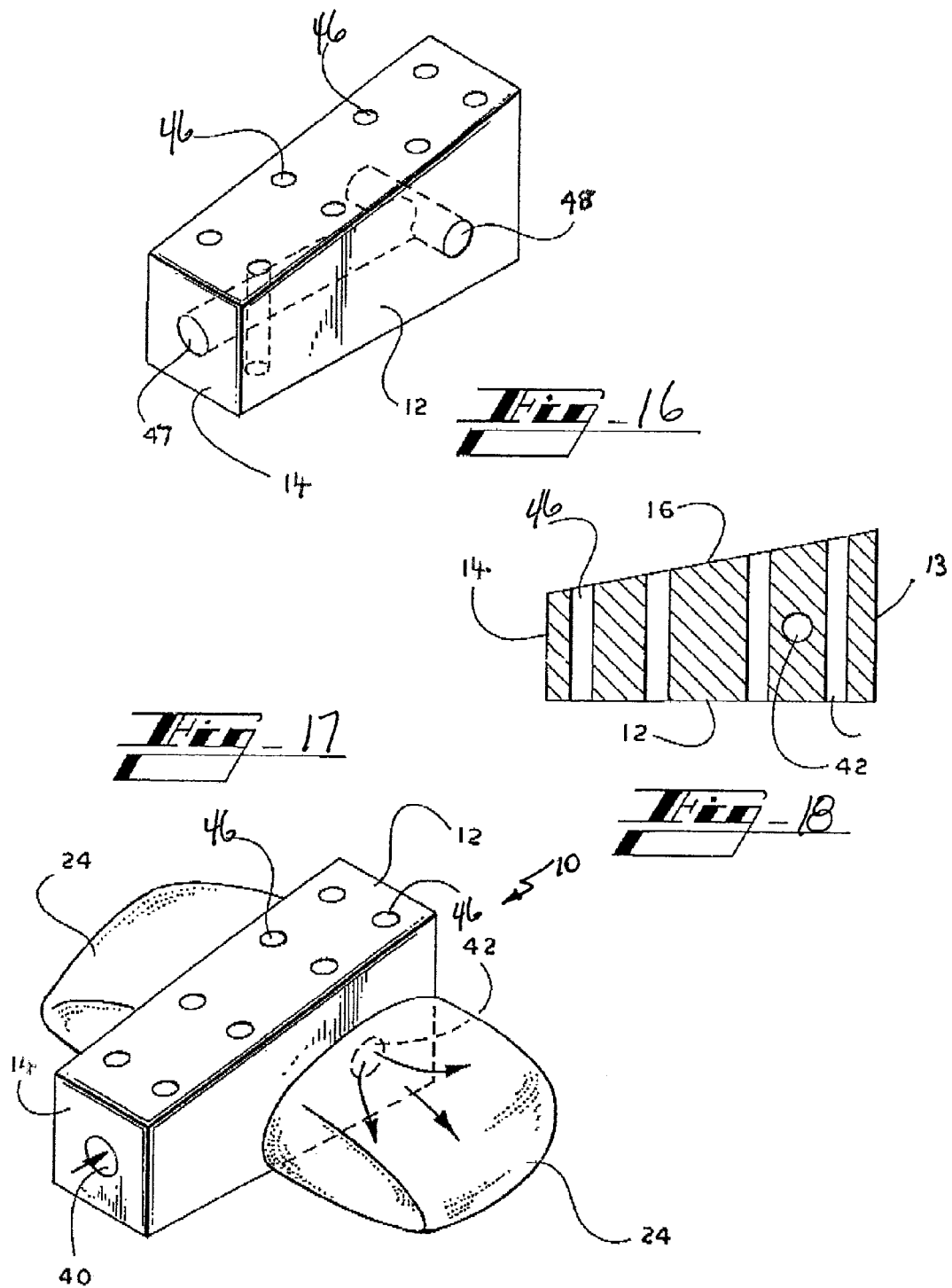

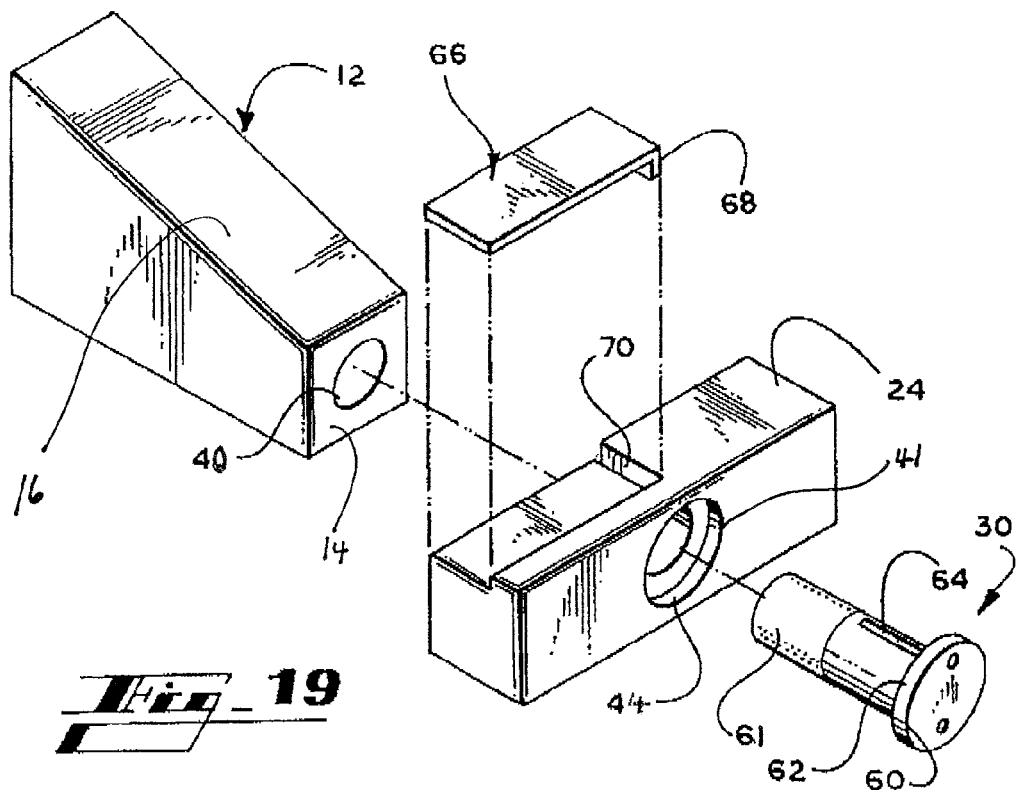
Fig_19
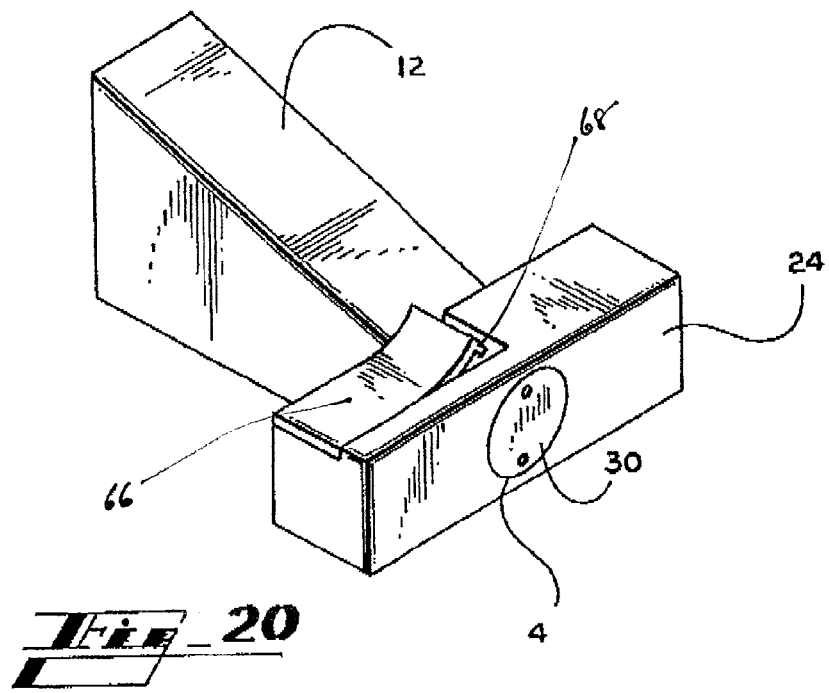
Fig_20

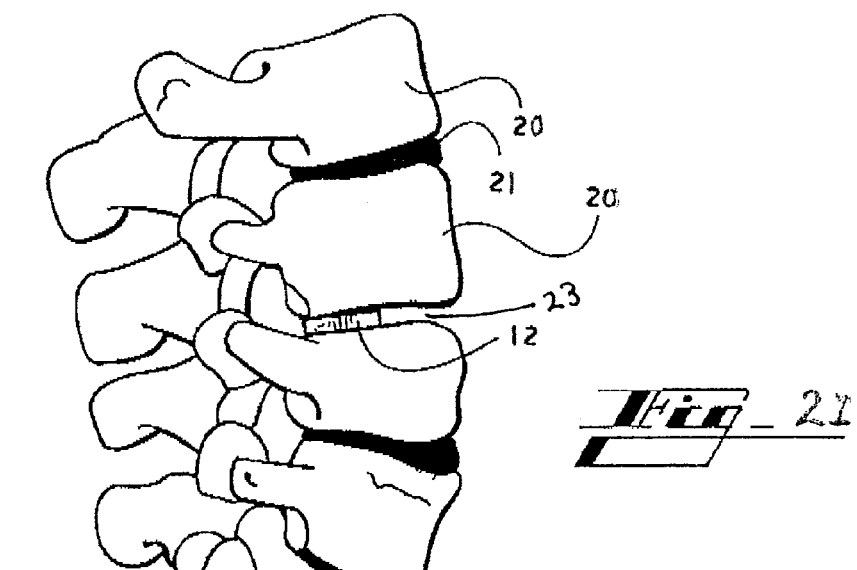
Fig_21
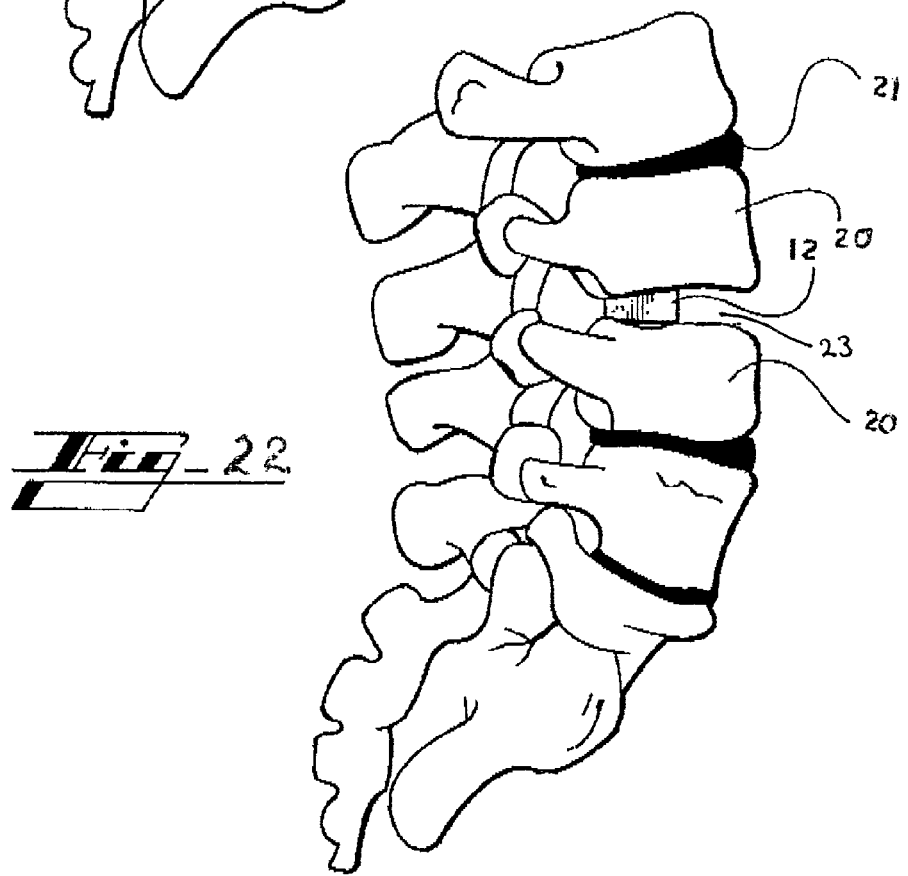
Fig_22

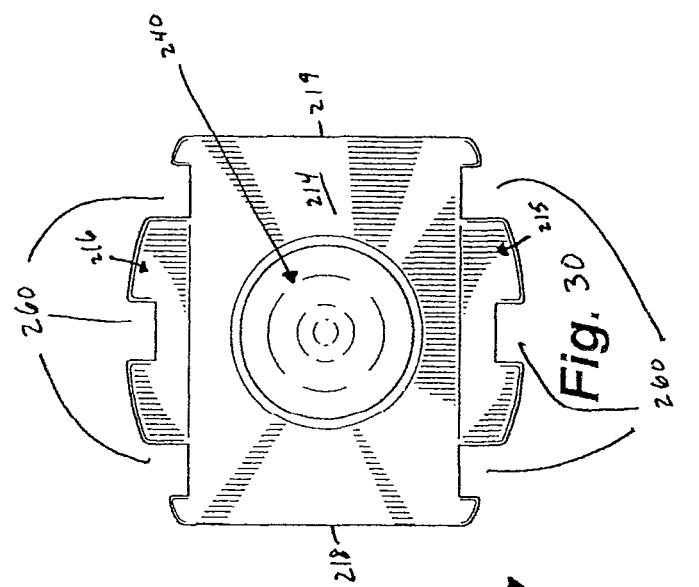
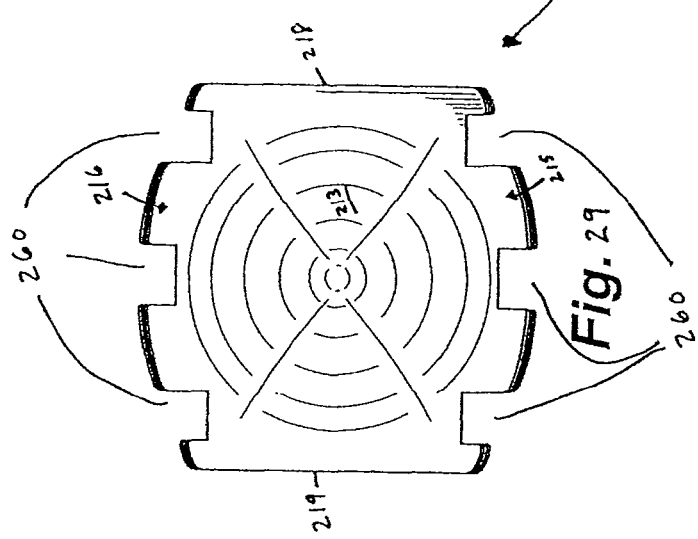

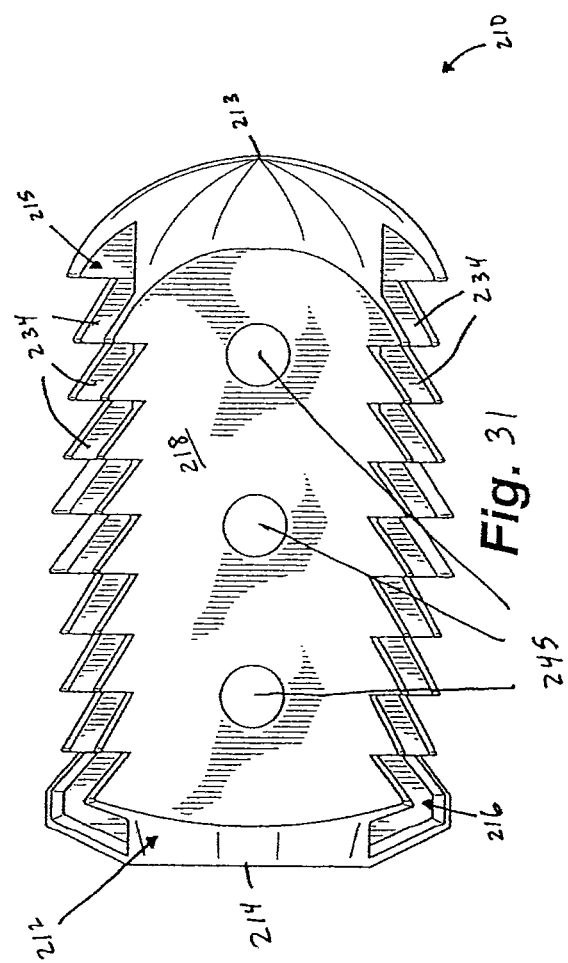

VERTEBRAL BODY REPLACEMENT AND METHOD OF USE

CROSS-REFERENCE TO RELATED APPLICATIONS

This application is a continuation of application Ser. No. 10/701,883, filed on Nov. 5, 2003; now abandoned which application is a continuation-in-part of application Ser. No. 09/941,040, filed Aug. 28, 2001; now abandoned which claims the benefit of provisional application No. 60/228,694, filed Aug. 29, 2000.

Application Ser. No. 10/701,883 is also a continuation-in-part of application Ser. No. 09/947,851, filed Sep. 6, 2001, now U.S. Pat. No. 6,824,565; which claims the benefit of provisional application No. 60/231,142, filed Sep. 8, 2000.

Application Ser. No. 10/701,883 also claims the benefit of provisional application No. 60/476,075, filed Jun. 5, 2003, the entirety of which is incorporated herein by reference.

INCORPORATION BY REFERENCE

The specification of application Ser. Nos. 10/701,883, 09/947,851, published under 20020045944; application Ser. No. 10/403,598, published under no. 20030171814; and application Ser. No. 09/941,040, published under no. 20020029082 are incorporated herein in their entirety, by this reference.

FIELD OF THE INVENTION

A vertebral body replacement is provided to be inserted into an intervertebral space to support the spinal column of a patient. The vertebral body replacement described herein also relates to methods for implanting the vertebral body replacement into the spinal column using an installation tool and securing the body replacement therein.

BACKGROUND OF THE INVENTION

The spinal column, which is the central support to the vertebrate skeleton and a protective enclosure for the spinal cord, is a linear series of bones, or vertebrae. Intervertebral discs separate and reduce friction between adjacent vertebrae and absorb compression forces applied to the spinal column. Spinal nerves that extend from each side of the spinal cord exit the column at intervertebral foramina.

A typical vertebra comprises an anterior body, and a posterior arch that surrounds the spinal cord lying within the vertebral foramen formed by the arch. The muscles that flex the spine are attached to three processes extending from the posterior arch. On the upper surface of each vertebra in a standing human, are two superior articulated processes that oppose two inferior articulated processes extending from the lower surface of an adjacent vertebra. Facets on the opposing processes determine the range and direction of movement between adjacent vertebrae, and hence the flexibility of the spinal column.

The intervertebral discs include the fibrillar cartilage of the anulus fibrosus, a fibrous ring, the center of which is filled with an elastic fibrogelatinous pulp that acts as a shock absorber. The outer third of the anulus fibrosus is innervated. The entire spinal column is united and strengthened by encapsulating ligaments.

Back pain is one of the most significant problems facing the workforce in the United States today. It is a leading cause of sickness-related absenteeism and is the main cause of disability for people aged between 19 and 45. Published reports suggest that the economic cost is significant, treatment alone exceeding $80 billion annually. Although acute back pain is common and typically treated with analgesics, chronic pain may demand surgery for effective treatment.

Back pain can occur from pinching or irritation of spinal nerves, compression of the spine, vertebral shifting relative to the spinal cord axis, and bone spur formation. The most common cause of disabling back pain, however, stems from trauma to a intervertebral disc, resulting from mechanical shock, stress, tumors or degenerative disease, which may impair functioning of the disc and limit spinal mobility. In many cases, the disc is permanently damaged and the preferred treatment becomes partial or total excision.

Another cause of back injury is herniation of the intervertebral disc, wherein the gelatinous fluid of the nucleus pulposus enters the vertebral canal and pressures the spinal cord. Again, surgery is often the only method available for permanent relief from pain or the neurological damage ensuing from the pressure of fluid on the spinal cord, and requires replacement of the damaged disc.

Traumatic injury to an intervertebral disc that is not removed will frequently promote scar tissue formation. Scar tissue is weaker than original healthy tissue so that the disc will progressively degenerate, lose water content, stiffen and become less effective as a shock absorber. Eventually, the disc may deform, herniate, or collapse, limiting flexibility of the spinal column at that position. The only option is for the intervertebral disc to be partially or totally removed.

When the disc is partially or completely removed, it is necessary to replace the excised material to prevent direct contact between hard bony surfaces of adjacent vertebrae. One vertebral body replacement that may be inserted between adjacent vertebrae, according to U.S. Pat. No. 5,989,291 to Ralph et al., includes two opposing plates separated by a belleville washer or a modified belleville washer. The washer functions to provide a restorative force to mimic the natural functions of the disc of providing a shock absorber and mobility between adjacent vertebrae. However, mechanical devices intended to replicate intervertebral disc function have had only limited success. An alternative approach is a "cage" that maintains the space usually occupied by the disc to prevent the vertebrae from collapsing and impinging the nerve roots.

Spinal fusion may be used to restrict the motion, between two vertebrae, that comes from segmental instability. Fusing the vertebrae together, however, reduces the mechanical back pain by preventing the now immobile vertebrae from impinging on the spinal nerve. The disadvantage of such body replacements is that stability is created at the expense of the flexibility of the spine.

Surgical procedures for replacing intervertebral disc material, rather than fusing of the vertebrae, have included both anterior approaches and posterior approaches to the spinal column. The posterior approach (from the back of the patient) encounters the spinous process, superior articular process, and the inferior articular process that must be removed to allow insertion of the disc replacement material into the intervertebral space. The excess removal of the bony process triggers further degradation and impediment of the normal movement of the spine. The anterior approach to the spinal column is complicated by the internal organs that must be bypassed or circumvented to access the vertebrae.

Many intervertebral body replacements require preparation of the surfaces of the adjacent vertebrae to accommodate the body replacement, causing significant tissue and bone trauma. For example, chiseling or drilling of the vertebral surface may be required to prepare a receiving slot. They may also require screwing the body replacement into the intervertebral space, making installation difficult and increasing trauma to the vertebral tissue. Many body replacements include complex geometries and are costly to manufacture. Examples of such geometrically complex body replacements are described in U.S. Pat. No. 5,609,636 to Kohrs et al., U.S. Pat. No. 5,780,919 to Zdeblick et al., U.S. Pat. No. 5,865,848 to Baker and U.S. Pat. No. 5,776,196 to Matsuzaki et al. Many of these complex body replacements may require screwing the body replacement into the intervertebral space, thereby making installation difficult and traumatic to the vertebral tissue.

SUMMARY OF THE INVENTION

There is a need for a vertebral body replacement having a simple geometry that can be easily inserted into an intervertebral space while causing minimal trauma to the surface of the vertebrae as well as the bony processes thereof. The present invention provides a vertebral body replacement having a simple geometry for supporting adjacent vertebrae after excision, at least partially or wholly, of an intervertebral disc. The body replacement includes a body having a lower surface and an upper surface. The lower surface will be supported by a lower vertebra; the upper surface will support the adjacent upper vertebra. The body of the vertebral body replacement of the present invention, therefore, provides support between the two adjacent vertebrae and to the spinal column.

The body of the vertebral body replacement of the present invention additionally has an anterior face and a posterior face extending from the lower surface. The height of the anterior face of the body may be greater than the height of the posterior face to maintain the curvature of the spine when the vertebral body replacement is inserted between two vertebrae. A stabilizing body is connected to and extends from the body of the body replacement. The stabilizing body may be connected to the body of the body replacement by an attachment member that optionally allows the body and the stabilizing body to rotate relative to each other. The present invention further provides a vertebral body replacement having a locking assembly whereby the body and the stabilizing body, once orientated to a desired position with a spinal column, and relative to each other, may be rigidly locked.

The present invention further contemplates the optional use of one or more channels extending through the body of the body replacement to facilitate tissue ingrowth and bony fusion between the adjacent vertebrae.

In one embodiment of the present invention, the stabilizing body may be formed by delivering a biocompatible liquid polymer material into a liquid receiving bore and a transverse bore. The polymer material is injected in an amount sufficient to fill the bore and to pass out of at least one transverse bore that communicates with the liquid receiving bore. The excess polymer seeps into the space between adjacent vertebrae. Hardening of the liquid polymer material then forms the stabilizing body extending from the body of the body replacement.

The present invention further provides a method of maintaining a separation distance between adjacent vertebrae. At least one vertebral body replacement according to the present invention can be inserted into an intervertebral space to support the adjacent vertebrae. The body of the vertebral body replacement may be inserted into the receiving intervertebral space in an orientation that reduces contact between the body replacement and the adjacent vertebrae. Once inserted into the selected position, the body of the vertebral body replacement may be rotated so that the lower surface and the upper surface of the body contact the adjacent vertebrae, whereupon the body is secured by attaching (if necessary) and locking the stabilizing body.

In another embodiment, a vertebral body replacement is provided having a shape resembling, in part, a bullet, football, or other oblong object. The vertebral body replacement of this embodiment includes a front end in a nose shape to provide a minimally invasive installation, serrations formed in the wall of the body replacement's body to prevent expulsion once the body replacement is in place, and a tapered asymmetric shape to provide spinal lordosis. The vertebral body replacement of this embodiment is typically used in pairs by placing flat faces of adjacent vertebral body replacements in planes parallel to and in near contact with one another. The vertebral body replacement of this embodiment also includes a threaded hole for assembly tooling, an integral protrusion to provide stability, and two window shaped passages extending generally from top to bottom through the body that are typically filled with bone tissue. The integral protrusion, in an exemplary embodiment, defines an arcuate face which appears as a "bloated" or bulbous protrusion and is formed to provide stability in the horizontal plane and prevents tilting or rotation within the plane. The integral stabilizing protrusion also acts to increase the bearing area to reduce contact pressure between the body replacement and the vertebral plate. The body is also provided with holes passing completely through the body, from side to side, to promote tissue growth.

In yet another embodiment, a vertebral body replacement is provided having a shape resembling, in part, a bullet, football, or other oblong object. The vertebral body replacement of this embodiment includes a front end in a nose shape to provide a minimally invasive installation, serrations formed in the wall of the body replacement's body to prevent expulsion once the body replacement is in place, and a tapered asymmetric shape to provide spinal lordosis. The vertebral body replacements of this embodiment are typically used in pairs by placing flat faces of adjacent vertebral body replacements in planes parallel to and in near contact with one another. The vertebral body replacement of this embodiment also includes a threaded hole for assembly tooling, two growth hole faces that are both flat, and two window shaped passages extending generally from top to bottom through the body that are typically filled with bone tissue. The body is also provided with holes passing completely through the body, from flat face to flat face, to promote tissue growth.

Various objects, features, and advantages will become more apparent upon review of the detailed description set forth below when taken in conjunction with the accompanying drawings.

BRIEF DESCRIPTION OF THE FIGURES

FIG. 1 is a perspective view of a vertebral body replacement according to one embodiment of the present invention.

FIG. 2 is an exploded perspective view of the vertebral body replacement of FIG. 1 showing the body replacement in an unassembled manner.

FIG. 3 is an end view of the embodiment according to FIG. 1.

FIG. 4 is a perspective view of another embodiment of the vertebral body replacement according to the present invention, illustrating a body rotatably connected to a stabilizing body.

FIG. 5 is a cross-sectional side view of the vertebral body replacement taken along lines 5-5 of FIG. 4.

FIG. 6 is a cross-sectional side view of an embodiment of the locking assembly comprising a locking pin.

FIG. 7 is an exploded perspective view of the vertebral body replacement of FIG. 4 showing the vertebral body replacement in an unassembled manner.

FIG. 8 is a perspective view of the vertebral body replacement according to FIG. 4 showing a preinsertion orientation relative to the stabilizing body.

FIG. 9 is a perspective view according to another embodiment of the vertebral body replacement of the present invention, showing triangular protrusions thereon.

FIG. 10 is a side view of the embodiment of the vertebral body replacement having triangular protrusions thereon.

FIG. 11 is a perspective view of another embodiment of the vertebral body replacement of the present invention, showing rounded protrusions thereon.

FIG. 12 is a side view of the embodiment of the vertebral body replacement having rounded protrusions.

FIG. 16 is a perspective view of an embodiment of the vertebral body replacement according to the present invention having channels and a liquid receiving bore and communicating traverse bore system for receiving a liquid polymer material.

FIG. 17 is a perspective view of the vertebral body replacement according to FIG. 16 showing a stabilizing body formed by a liquid polymer material extruded from a traverse bore and hardening in situ.

FIG. 18 is a cross-sectional view of the vertebral body replacement according FIG. 16.

FIG. 19 is an exploded view of an embodiment of the vertebral body replacement of the present invention having a leaf spring locking assembly.

FIG. 20 is a perspective view of the assembled vertebral body replacement having a leaf spring locking assembly.

FIG. 21 is a side-elevation of the lower region of the human spinal column, showing the body of the vertebral body replacement according to the present invention inserted between adjacent vertebrae and before rotation to substantially contact adjacent vertebrae.

FIG. 22 is a side-elevation of the lower region of the human spinal column, showing the body of the vertebral body replacement according to the present invention rotated to contact and support adjacent vertebrae.

FIG. 29 is a front view of the vertebral body replacement of FIG. 27.

FIG. 30 is a rear view of the vertebral body replacement of FIG. 27.

FIG. 31 is left side view of the vertebral body replacement of FIG. 27.

DETAILED DESCRIPTION OF THE INVENTION

Figure 13:
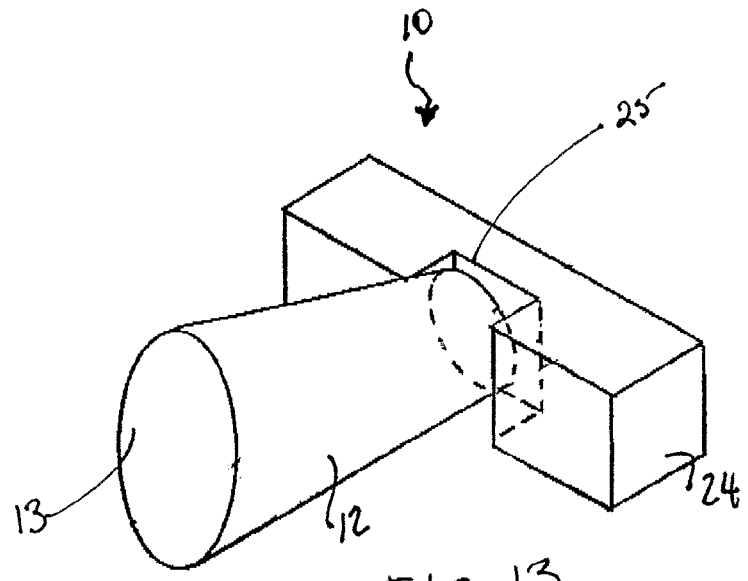
FIG. 13 is a perspective view of an embodiment of the vertebral body replacement according to the present invention having an ellipsoidal body.

A full and enabling disclosure of the present invention, including the best mode known to the inventor of carrying out the invention, is set forth more particularly in the remainder of the specification, including reference to the accompanying drawings, wherein like reference numerals designate corresponding parts throughout several figures. This description is made for the purpose of illustrating the general principles of the invention and should not be taken in the limiting sense.

Examples of the vertebral body replacement 10 in accordance with the present invention are shown in FIGS. 1-20. As shown in FIG. 22, the vertebral body replacements 10 of the present invention support adjacent vertebrae 20 after partial or total surgical excision of an intervertebral disc 21, thereby preventing collapse and/or compression in this region of the spine that might otherwise lead to sever neurological damage. The vertebral body replacement 10 of the present invention is useful to replace an intervertebral disc 21 that has degenerated due to traumatic injury, vertebral displacement, disease such as, for example, autoimmune disease or rheumatoid arthritis or any other pathological condition of the spinal column that may injure or shift the intervertebral disc. The vertebral body replacements 10 of the present invention provide support to the vertebrae 20 and maintain the distance between vertebrae and preserve the natural curvature of the spine.

The vertebral body replacement 10 of the present invention includes a body 12 having a first bore 40, as shown in FIGS. 2 and 3. The body 12 is adapted to fit within an intervertebral space 23 between adjacent vertebrae 20. A stabilizing body 24 having a second bore 41 with an interior surface 44 extends from the body 12 and is adapted to retain the body 12 within the intervertebral space 23. The body 12 may be attached to the stabilizing body 24 by an attachment member 30. The stabilizing body 24 may be rotatably attached to the body 12 by slideably disposing the attachment member 30 through the second bore 41 of the stabilizing body 24. It is contemplated that the stabilizing body 24 may be optionally attached to the body 12, and connected thereto by the attachment member 30 before inserting the vertebral body replacement 10 into a patient. Alternatively, the stabilizing body 24 may be attached after the body 12 has been inserted into the patient.

The attachment member 30 may be any device that will connect the body 12 to the stabilizing body 24. Suitable devices particularly useful in the present invention, however, include a pin, a bolt, a threaded pin or bolt and the like. One example of an attachment member 30 is shown in FIG. 2 comprising a shaft 26 and a head 27. In another example, shown in FIG. 6, the attachment member 30 comprises an anchoring region 28, a rotating region 29, and a head 27. It is contemplated, however, that the anchoring region 28 may be threaded for engaging a like thread in the first bore 40 for securing the anchoring region 28 therein. It is also contemplated that any means known to one of skill in the art may be employed to secure the anchoring region 28 to the body 12 including, but not limited to, interlocking screw threads, an adhesive, a leaf spring lock or any other method that will rigidly connect the body 12 to the attachment member 30.

Once the body 12 has been rotated into the desired position relative to the adjacent vertebrae 20, the stabilizing body may be attached to the body 12, or if already attached thereto, the vertebral body replacement 10 may be locked to form a rigid assembly. In one embodiment of the vertebral body replacement 10 of the present invention, as shown in FIGS. 1-3, the body 12 may enter a recess 25 of the stabilizing body 24, the recess resisting further rotation of the body 12 relative to the stabilizing body 24.

It is contemplated that the vertebral body replacement 10 may be of any biocompatible or physiologically inert material or combination of such materials having the mechanical strength capable of maintaining the intervertebral space 23 between two adjacent vertebrae 20 when inserted therein. The material of the body 12 and stabilizing body 24 of the vertebral body replacement 10 of the present invention may or may not be identical and may be rigid such as a metal, a rigid plastic or the like. Examples of such materials include bone, titanium, titanium alloy, stainless steel, chrome cobalt, and polymeric materials such as methyl methacrylate (MMA), urethane, polyacetal and the like. The material of the vertebral body replacement 10 may, however, also have a degree of resilience and thereby tolerate a degree of compression. Such materials may include, but are not limited to, polymers such as carbon fiber reinforced polymer such as PEEK (polyetherether ketone), polycarbonate, polypropylene, polyethylene, polyamide and silicone-based polymers.

Figure 14:
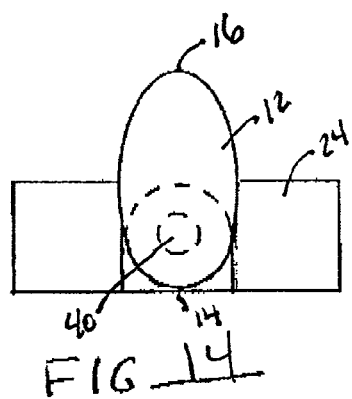
FIG. 14 is an end view of the vertebral body replacement having an ellipsoidal body.
Figure 15:
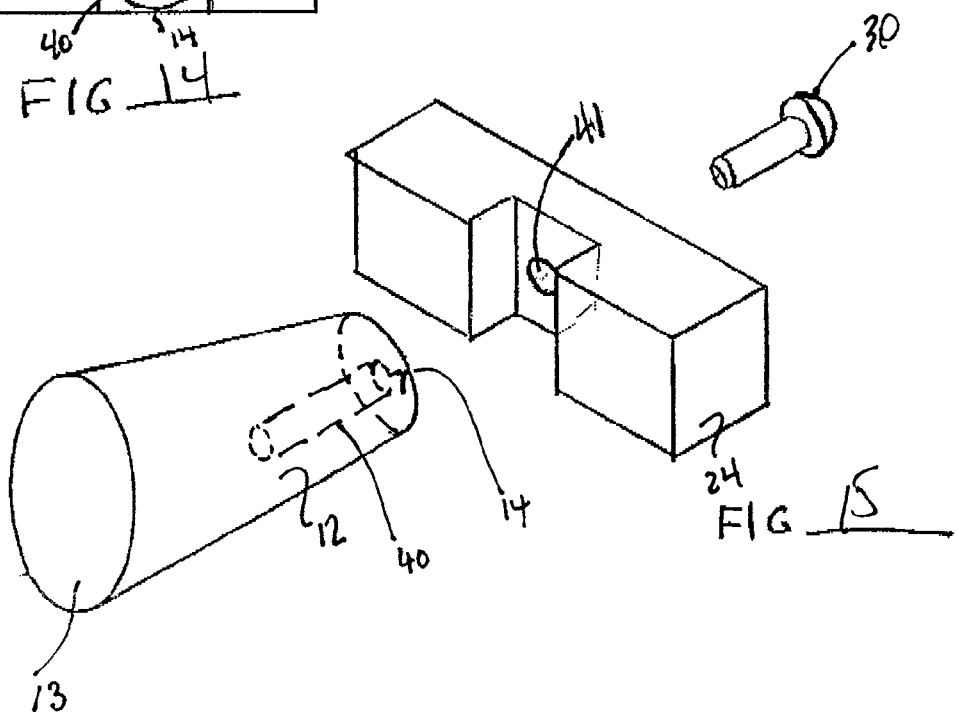
FIG. 15 is an exploded perspective view of the vertebral body replacement having an ellipsoidal body, showing the vertebral body replacement in an unassembled manner.

The body 12 of the vertebral body replacement 10 of the present invention may have any conformation that will allow the body 12 to be positioned in an intervertebral space 23 between adjacent vertebrae 20 and will subsequently maintain an intervertebral space when in a desired position. Suitable geometric cross-sections that may be applied to the body 12 include, for example, a rectangular cross-section, a trapezoidal cross-section, a circular cross-section, an elliptical cross-section or the like. In one embodiment of the vertebral body replacement 10 of the present invention, the body 12 has a rectangular transverse cross-section as shown, for example, in FIGS. 1-3. In another embodiment of the vertebrate body replacement of the present invention alternative configuration, the body 12 may have an anterior face 13 and a posterior face 14 and have a circular or an ellipsoidal cross-section, as shown in FIGS. 13-15, or a combination thereof.

The vertebral body replacement 10 of the present invention may have a plurality of surfaces, including a lower surface 15 and an upper surface 16, the lower surface 15 having an anterior face 13 and a posterior face 14 extending therefrom, as shown in FIG. 1. The anterior face 13 may be directed towards the inner body cavity of a patient, and the posterior face 14 may be directed towards the dorsal surface of the patient. The vertebral body replacement 10 can be configured such that the height of the anterior face 13 is greater than the height of the posterior face 14, as is illustrated, for example, in FIG. 1. The difference in the height of the opposing anterior 13 and posterior 14 faces of the vertebral body replacement 10 of the present invention, so that the lower surface 15 and the upper surface 16 are non-parallel, is useful to preserve the natural curvature of the spinal column.

The body 12 of the vertebral body replacement 10 of the present invention may further include a channel 46 or a plurality of channels 46 extending through the body 12 such as, for example, shown in FIGS. 16-18. Bony or other tissue growth from adjacent vertebrae 20 that extends into the channels 46 of the vertebral body replacement 10 of the present invention may unite and effectively fuse the adjacent vertebrae 28. It is further contemplated that a tissue growth factor or an osteogenic material may be inserted into the apertures to facilitate this fusion. Suitable growth factors include, but are not limited to, growth hormones, steroids, tissue growth factors and the like. Alternatively, the channel 46 or plurality of channels 46 may only partially extend into the body 12. While not fusing the adjacent vertebrae 20, therefore, the penetrating tissue growth will stabilize the vertebral body replacement 10 within the intervertebral space 23.

The lower surface 15 and the upper surface 16 of the vertebral body replacement 10 optionally includes at least one protrusion 34 on the lower surface 15 and/or on the upper surface 16 for frictionally engaging the adjacent vertebrae 20. Exemplary embodiments of the protrusions 34 of the present invention are illustrated in FIGS. 9-12. It is contemplated that the body 12 may have a single protrusion 34, or a plurality of protrusions 34 as shown in FIGS. 9-12. The protrusions 34 may have any suitable geometric configuration that will allow the body 12 of the vertebral body replacement 10 of the present invention to be secured to adjacent vertebrae 20, including having a triangular, rounded, or rectangular cross-section and the like, or any combination thereof. The protrusions may be elongated as shown in FIGS. 9-12, or any other shape such as square or circular protrusions or irregular protrusions not elongated.

As shown in FIGS. 6-8, 19 and 20, embodiments of the vertebral body replacement 10 of the present invention may further include a locking assembly whereby, once the vertebral body replacement 10 has been inserted into an intervertebral space and the body 12 has been rotated into a desired position, the body 12 is locked relative to the stabilizing body 24. In one exemplary embodiment of the vertebral body replacement 10 of the present invention, the locking assembly is a locking pin 50 having a male member 51, a female member 52, the female member 52 having a lumen 53, and a spring 54 therein. The male member 51 is slideably disposed within the lumen 53 of the female member 52. When the male member 51 is pushed into the lumen 53, it encounters a resistant force exerted by compression of the spring 54.

In the embodiment of the vertebral body replacement 10 of the present invention, as shown in FIG. 6, the body 12 further includes a first pin receiving bore 42 capable of accepting the female member 52 of the locking pin 50. The stabilizing body 24 has a second pin receiving bore 43 capable of receiving the male member 51 of the locking pin 50.

Rotation of the body 12 relative to the stabilizing body 24 by rotation of the rotating region 29 of the attachment member 30 within the second bore 41, aligns the first pin receiving bore 42 and the second pin receiving bore 43. The compressed spring 54 will expand and push the male member 51 of the locking pin 50 partially into the second pin receiving bore 43, thereby preventing further rotation of the body 12 relative to the stabilizing body 24. In an alternative exemplary embodiment of the present invention, the male member 51 of the locking pin 50 is within the second pin receiving bore 43. The first pin receiving bore 42 receives the female member 52 of the locking pin 50.

In yet another embodiment of the vertebral body replacement 10 of the present invention, the first pin receiving bore 42 of the body 12 has a spring 54 therein and a locking pin 50 that upon alignment of the first and the second pin receiving bores, 42 and 43 respectively, will push the locking pin 50 into the first pin receiving bore 42. A portion of the locking pin 50 is retained within the second pin receiving bore 43, thereby locking movement of the body 12 relative to the stabilizing body 24.

In still another embodiment of the vertebral body replacement 10 of the present invention, as schematically illustrated in FIGS. 19 and 20, the stabilizing body 24 of this embodiment further includes a locking assembly having a communicating slot 70 connecting surface 17 of the stabilizing body 24 and the interior surface 44 of the second bore 41. Attached to the surface 17 is a leaf spring 66 having a locking arm 68 capable of slideably entering through the communicating slot 70, and thereby extending into the interior of the second bore 41. This embodiment of the present invention further comprises the attachment member 30 having an anchoring region, the rotating region 29 and a head 27. The rotating region 29 has a receiving notch 64 configured to receive the locking arm 68 of the leaf spring 66.

The attachment member 30 is initially positioned so that the locking arm 68, which is slideably disposed in the communicating slot 70, and the receiving notch 64 are not aligned. The body 12 and the attachment member 30 secured thereto may be rotated relative to the stabilizing body 24 to place the body 12 in a desired position within the intervertebral space 23. The rotation will align the locking arm 68 and the receiving notch 64 whereupon the leaf spring 66 will depress the locking arm 68 into the receiving notch 64, and locking the body 12 and the stabilizing body 24 into the selected configuration.

In another embodiment of the vertebral body replacement 10 of the present invention, the stabilizing body 24 extending from the body 12 is a hardened biocompatible liquid delivered to the body 12 of the vertebral body replacement 10 once the vertebral body replacement 10 has been inserted in the spinal column of the patient. Referring now to FIGS. 16-18, in this embodiment, the body 12 has a liquid receiving bore 47 that extends from the posterior face 14 of the body 12 to an intermediate position within the body 12. It is further contemplated, however, that the liquid receiving bore 47 may extend from any surface of the body 12 that will allow delivery of a liquid thereto. The body 12 further includes at least one transverse bore 48 communicating with the liquid receiving bore 47 and with an exterior surface of the body 12.

In this embodiment, once the vertebral body replacement 10 is inserted between the adjacent vertebrae 20, a biocompatible liquid polymer material is delivered into the liquid receiving bore 47 in an amount greater than the volume of the liquid receiving bore 47. Excess liquid polymer material flows from the liquid receiving bore 47 into the communicating transverse bore 48 and subsequently passes out of the transverse bore 48 into the intervertebral space 23, whereupon it hardens and forms the stabilizing portion 24 extending from the body 12.

As contemplated herein, the polymer material is biocompatible with the tissues of the patient, and has a viscosity that allows flow of the liquid polymer material through the liquid receiving bore 47 and the at least one traverse bore 48. An example of such a polymeric material that is useful in the present invention is methyl methacrylate. Curing of the liquid polymer material may occur naturally by, for example, exposing the polymer material to ambient conditions, or it may require, for instance, activation through an ultraviolet, chemical or other appropriate source.

Another aspect of the present invention is a method of inserting the vertebral body replacement 10 of the present invention between adjacent vertebrae 20 of the spine to facilitate stabilizing the spine. Removal of at least a portion of an intervertebral disc 21 provides a gap for insertion of the vertebral body replacement 10 therein. A portion of an adjacent vertebra 20 may also require removal to more readily accommodate the vertebral body replacement 10. The slot where a portion of the vertebra and disc has been removed is defined herein as a vertebral body replacement receiving slot.

The direction of insertion of the vertebral body replacement 10 is selected by the surgeon according to the needs of the patient. The vertebral body replacement 10 may be inserted posteriorly as shown, for example in FIG. 21, anteriorly, or laterally relative to the spinal column. The body 12 of the vertebral body replacement 10 may be oriented such that during the insertion procedure the lower surface 15 and the upper surface 16 of the body 12 are normal to the adjacent vertebrae 20 and substantially out of contact with vertebral surfaces. Once inserted into a desired position in the intervertebral space 23, as shown in FIG. 22, the body 12 of the vertebral body replacement 10 of the present invention may be rotated so that the lower surface 15 and the upper surface 16 of the body 12 are substantially contacting the adjacent vertebrae 20. For example, the lower surface 15 of the vertebral body replacement 10 may then be in contact with the lower vertebra 20, and the upper surface 16 may support the adjacent upper vertebra 20. Optional protrusions 34 extending from the lower surface 15 and/or the upper surface 16 increase the frictional resistance between the body 12 and the adjacent vertebrae 20. The anterior face 13 of the body 12 is positioned relative to the spine to maintain a desired curvature thereof, as shown in FIGS. 21 and 22.

FIGS. 23-26 show another embodiment of a vertebral body replacement. Unless otherwise noted, the vertebral body replacement of this embodiment can be formed of, and in the manner of, any of the materials and methods as described above. For consistency, the elements labeled herein correspond as closely as possible to analogous elements of other embodiments.

Figure 23:
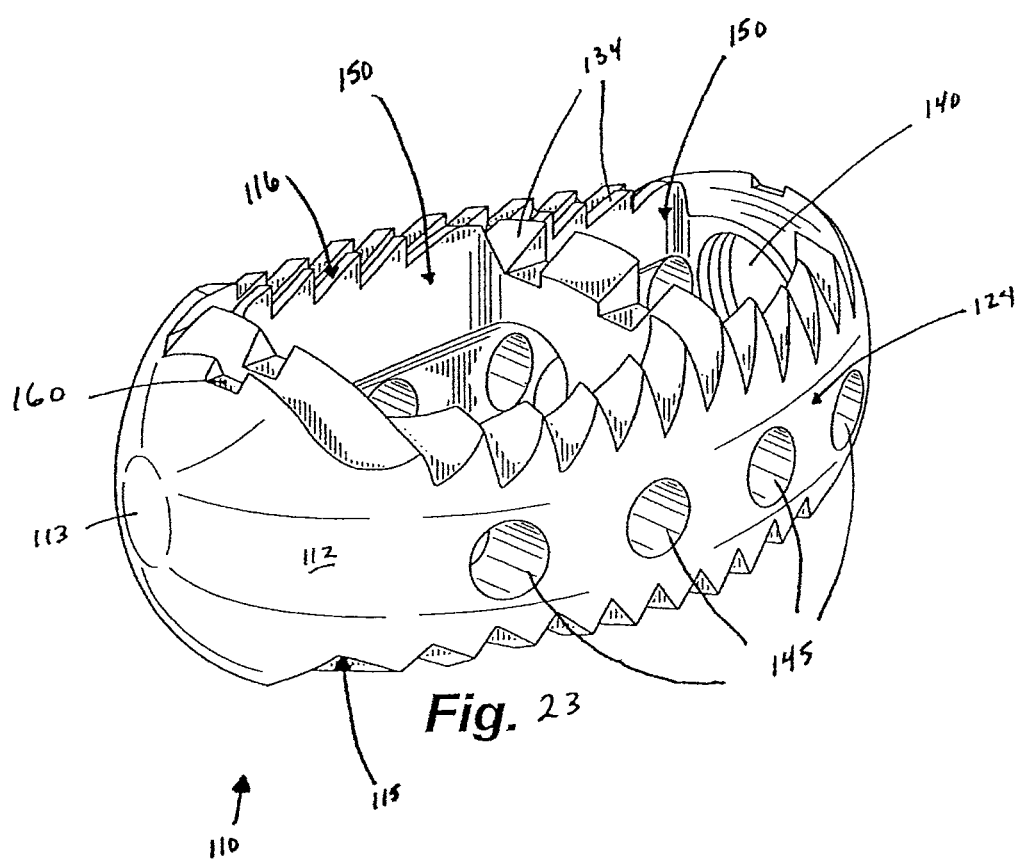
FIG. 23 is a three-dimensional representation of a vertebral body replacement according to another embodiment.

FIG. 23 shows a vertebral body replacement 110 that appears in rear view (FIG. 24) somewhat like a bullet tip and in side view (FIG. 26) somewhat like an American football or other oblong object. While FIGS. 23-26 represent a preferred shape and defined features of this embodiment, its exact appearance is acceptably modified so long as it performs the functions as described herein.

Figure 24:
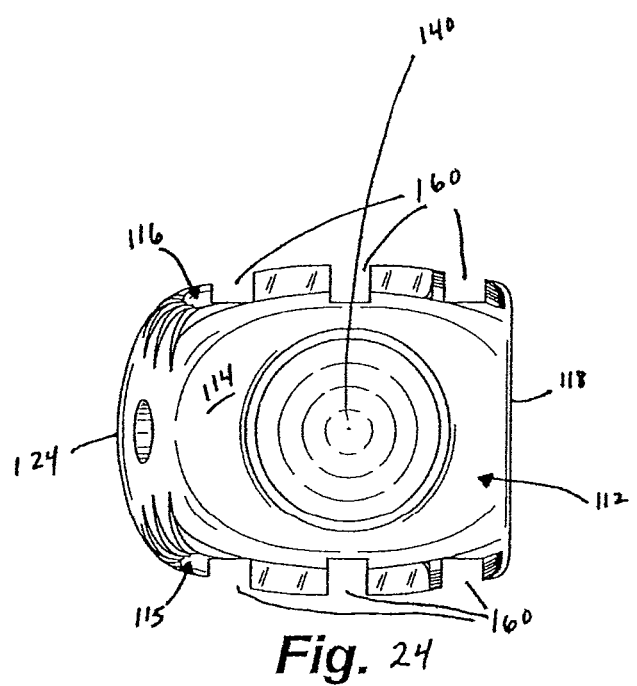
FIG. 24 is a rear view of the vertebral body replacement of FIG. 23.
Figure 25:
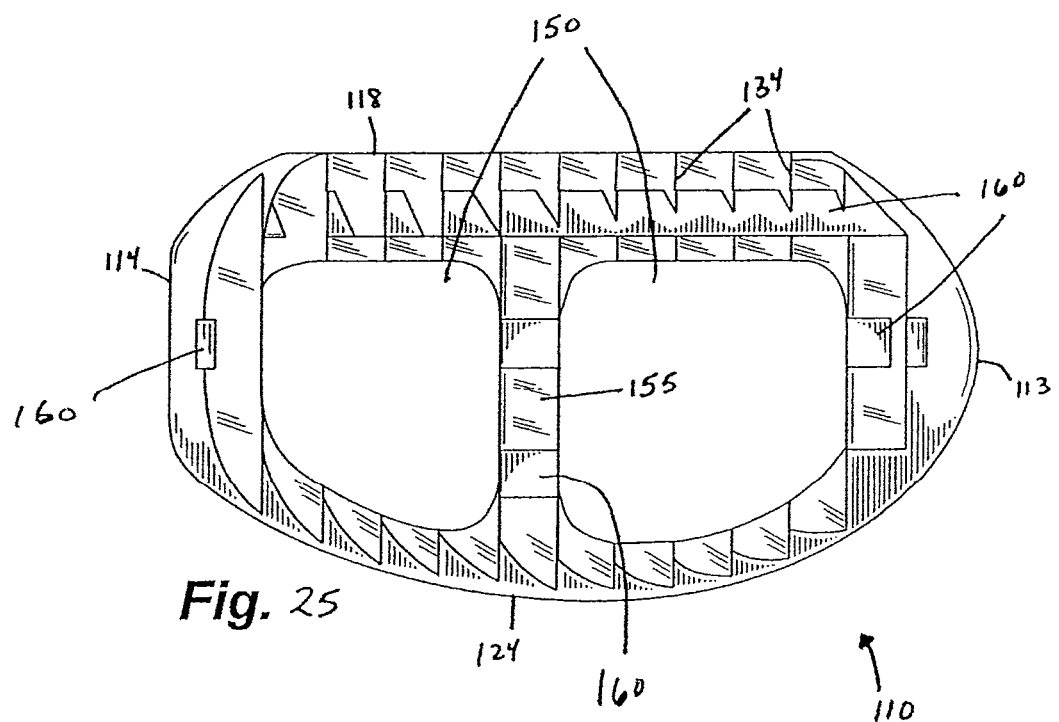
FIG. 25 is a bottom view of the vertebral body replacement of FIG. 23.

As shown in FIGS. 23 and 24, the vertebral body replacement 110 comprises a body 112, with front or anterior face 113, rear or posterior face 114, bottom 115, top 116, one flat face 118, and one curved or arcuate face 124. The arcuate face 124 appears as a "bloated" or bulbous protrusion and is formed to provide stability in the horizontal plane and prevents tilting or rotation within the plane. As shown in FIGS. 23, 24, and 25, the top 116 and bottom 115 have three grooves 160 formed therein that are parallel to the flat face 118 and that extend through serrations 134, from the posterior face 114 to the anterior face 113. The grooves 160 are useful for insertion tooling with the left-most groove extending continuously through the body 112 and the serrations 134 adjacent the flat face 118. The center and the right-most grooves begin on one side of window-shaped passages 150a, 150b and continue on the other side of the window-shaped passages 150a, 150b. The grooves 160 are shown herein as three grooves, but could be of any number that would facilitate the insertion of the vertebral body replacement 110 by a channel insertion tool. U.S. patent application Ser. No. 10/403,598, published under no. 20030171814, which is co-owned by the present inventors, details an insertion tool useful for installing a vertebral body replacement such as the one of the present embodiment and also details the method of installing a vertebral body replacement through the use of installation tools. U.S. patent application Ser. No. 10/403,598, published under no. 20030171814 is incorporated herein by reference as if the entirety of the application was reproduced herein.

FIGS. 23 and 24 also show a tooling hole 140 that is provided in the posterior face 114 for assembly tooling. The tooling hole 140 can be threaded if desired to assist in assembly. Alternately, the vertebral body replacement 110 of this embodiment is formed without the grooves 160 and/or without the tooling holes 140, for embodiments which are used with tooling or insertion methods that do not require such grooves and/or tooling hole.

FIG. 25 shows a bottom view of the vertebral body replacement 110 of FIG. 23 (the top being similar thereto and readily observed from FIG. 23). FIG. 25 shows the body 112 with posterior face 114 and anterior face 113. FIG. 25 also shows that the window-shaped passages 150a, 150b pass completely through the body 112. Spaced between the window-shaped passages 150a, 150b is a support 155 that is typically formed at the same time and from the same material as body 112. Support 155 divides the window-shaped passages 150a, 150b into two hollow cavities that are typically filled with bone tissue upon insertion of the body replacement during implant. The vertebral body replacement 110 also includes serrations 134 formed in the top 116 and bottom 115. FIG. 25 shows the serrations 134 from a bottom view and also shows the arcuate face 124, which is formed as an integral protrusion to provide stability.

Figure 26:
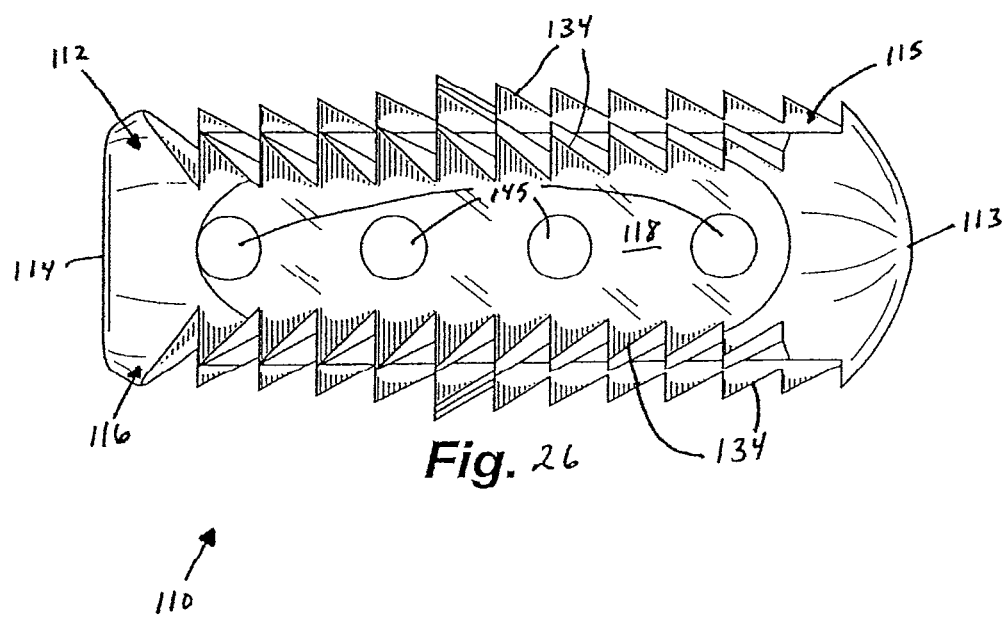
FIG. 26 is a left side view of the vertebral body replacement of FIG. 23.

FIG. 26 shows a side view of the vertebral body replacement 110 of FIG. 23. FIG. 26 shows the body 112, anterior face 113, posterior face 114, flat face 118, top 116, and bottom 115. Top 116 and bottom 115 are shown with serrations 134 extending most of the length thereof. The serrations 134 are shown each in the shape of a triangular saw tooth and are formed in body 112 to prevent expulsion once the vertebral body replacement 110 is in place. Although the vertebral body replacement 110 of the present embodiment is shown with the serrations 134 as described above, other gripping surfaces that perform the same function are acceptable. Also as seen in FIG. 26, top 116 and bottom 115 are tapered in an asymmetric shape to provide spinal lordosis. The anterior face 113 is in a curved shape to provide for minimally invasive installation. The body 112 is shown in FIG. 26 with four tissue growth holes 145a-145d formed in the flat face 118 and four tissue growth holes 145e-145h formed in the arcuate face 124. These holes 145 promote growth of tissue therein.

In application, the vertebral body replacements 110 of the present embodiment are typically used in pairs by placing the flat face 118 of one vertebral body replacement 110 and the flat face 118 of an adjacent vertebral body replacement 110 in parallel planes in near contact (not shown). Thus, since the arcuate face 124 is formed as an integral protrusion that is lop-sided and asymmetrical, the applied pair of vertebral body replacements will have protrusions on both sides. In one embodiment, each of the vertebral body replacements 110 of the pair are identical to each other and the pair are oriented up-side-down relative to one another. According to one example of the application of the vertebral body replacement, the pair of vertebral body replacements together resemble a generally circular top planar view and are of a size which approaches (while remaining smaller than) the size of the concavity of the particular vertebral plate upon which the pair is being applied. The thickness is chosen, according to one example of use, to provide replacement for a natural disc to occupy the intended inter-vertebral space (or so much of that thickness as is medically desired), bearing in mind the tapering for spinal lordosis. In commercial embodiments, a variety of sizes (e.g., widths and "diameters") may be produced and a pair matching as close as possible the needs of a particular patient may be selected and applied.

FIGS. 27-31 show yet another embodiment of a vertebral body replacement. Unless otherwise noted, the vertebral body replacement of this embodiment can be formed of, and in the manner of, any of the materials and methods as described above. For consistency, the elements labeled herein correspond as closely as possible to analogous elements of other embodiments.

Figure 27:
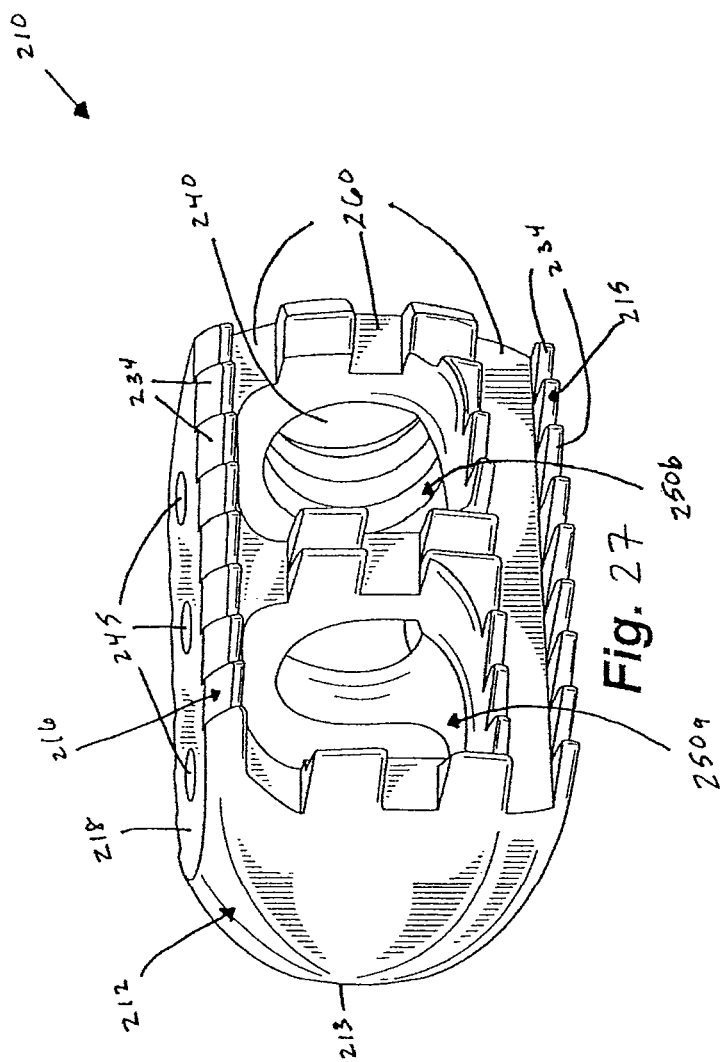
FIG. 27 is a three-dimensional representation of a vertebral body replacement according to yet another embodiment.
Figure 28:
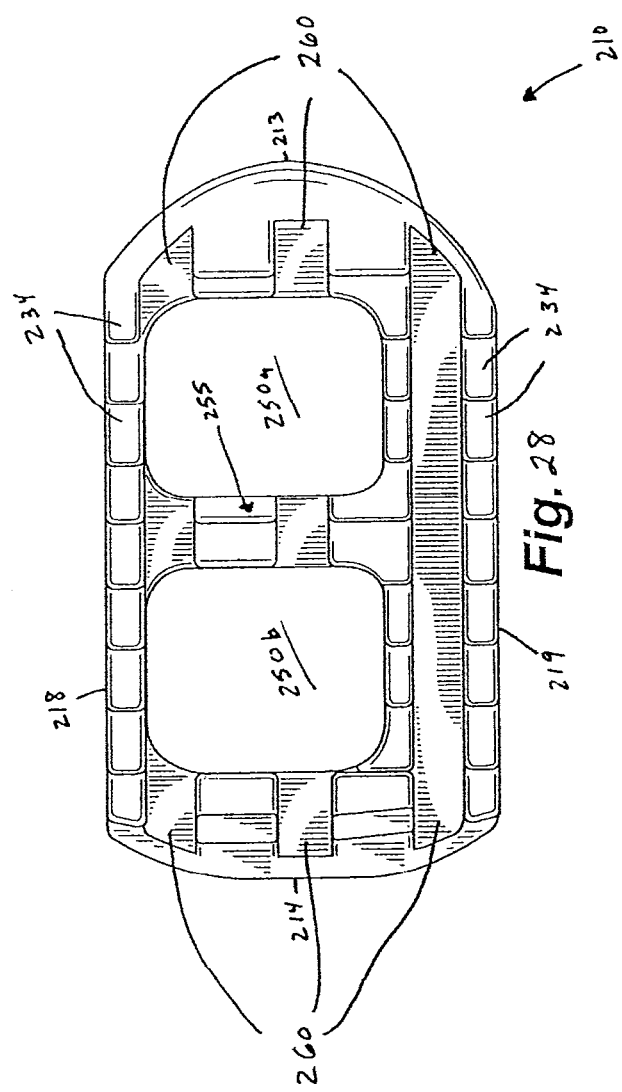
FIG. 28 is a bottom view of the vertebral body replacement of FIG. 27.

FIGS. 27, 28, and 31 show a vertebral body replacement 210 with a somewhat bullet shaped tip and in side view (FIG. 31) appears somewhat like an American football or other oblong object. While FIGS. 27-31 represent a preferred shape and defined features of this embodiment, its exact appearance is acceptably modified so long as it performs the functions as described herein.

As shown in FIGS. 27 and 28, the vertebral body replacement 210 comprises a body 212, with front or anterior face 213, rear or posterior face 214, bottom 215, top 216, and two flat faces 218 and 219. As shown in FIGS. 27-30, the top 216 and bottom 215 have three grooves 260 formed therein that are parallel to the flat faces 218 and 219. The grooves 260 extend through serrations 234, from the posterior face 214 to the anterior face 213. The grooves 260 are useful for insertion tooling with the left-most groove extending continuously through the body 212 and the serrations 234 adjacent the flat face 219. The center and right-most grooves begin on one side of window-shaped passages 250A, 250B and continue on the other side of window-shaped passages 250A, 250B. The grooves 260 are shown herein as three grooves, but could be of any number that would facilitate the insertion of the vertebral body replacement 210 by a channel insertion tool. As described in reference to an above embodiment, U.S. patent application Ser. No. 10/403,598, published under no. 20030171814, also by the present inventors, details an insertion tool useful for installing a vertebral body replacement, such as the one of this present embodiment, and also details the method of installing such a vertebral body replacement through the use of installation tools.

FIGS. 27 and 30 show a tooling hole 240 that is provided in the posterior face 214 for assembly tooling. The tooling hole 240 can be threaded if desired to assist in assembly. Alternately, the vertebral body replacement 210 of this embodiment is formed without the grooves 260 and/or without the tooling hole 240 if the vertebral body replacement 210 does not require such grooves and/or tooling hole for insertion.

FIG. 28 shows a bottom view of the vertebral body replacement 210 of FIG. 27 (the top being similar thereto and readily observed from FIG. 27). FIG. 28 shows the body 212 with posterior face 214 and anterior face 213. FIG. 28 also shows that the window-shaped passages 250A, 250B pass completely through the body 212. Spaced between the window-shaped passages 250A, 250B is a support 255 that is typically formed at the same time and from the same material as body 212. Support 255 divides the window-shaped passages 250A, 250B into two hollow cavities that are typically filled with bone tissue upon insertion of the vertebral body replacement 210 during implant. The vertebral body replacement 210 also includes serrations 234 formed in the top 216 and bottom 215. FIG. 28 shows the serrations 234 from a bottom view.

FIGS. 29 and 30 show the anterior face 213 and posterior face 214 with grooves 260 formed in the top 216 and bottom 215. FIGS. 29 and 30 also show flat faces 218 and 219. FIG. 30 shows tooling hole 240.

FIG. 31 shows a side view of the vertebral body replacement 210 of FIG. 27. FIG. 31 shows the body 212, anterior face 213, posterior face 214, flat face 218, top 216, and bottom 215. Top 216 and bottom 215 are shown with serrations 234 extending most of the length thereof. The serrations 234 are shown each in the shape of a triangular saw tooth and are formed in body 212 to prevent expulsion once the vertebral body replacement 210 is in place. Although the vertebral body replacement 210 of the present embodiment is shown with the serrations 234 as described above, other gripping surfaces that perform the same function are acceptable. Also as seen in FIG. 31, top 216 and bottom 215 can be tapered in an asymmetric shape to provide spinal lordosis. The anterior face 213 is in a curved shape to provide for minimally invasive installation. The body 212 is shown in FIG. 31 with three tissue growth holes 245A-245C formed in the flat faces 218 and 219. These holes 245 extend through the flat faces 218 and 219 and promote the growth of tissue therein.

In application, the vertebral body replacements 210 of the present embodiment are typically used in pairs by placing two vertebral body replacements 210 side by side with either of flat faces 218 or 219 adjacent and in parallel planes to nearly contact (not shown). The thickness of the pair of vertebral body replacements 210 installed is chosen, according to one example of use, to provide replacement for a natural disc to occupy the intended intervertebral space (or so much of that thickness as is medically desired), bearing in mind the tapering for spinal lordosis. In commercial embodiments, a variety of sizes (e.g., widths and "diameters") may be produced and a pair matching as close as possible the needs of a particular patient may be selected and applied.

In addition to the vertebral body replacement embodiments detailed above, the vertebral body replacements detailed in copending U.S. patent application Ser. No. 09/941,040, published under no. 20020029082, also by the present inventors, is hereby incorporated by reference as if the application is reproduced in its entirety herein. U.S. patent application Ser. No. 10/403,598, published under no. 20020029082 includes alternate vertebral body replacement embodiments that are capable of being inserted into intervertebral spaces through the use of insertion tools, such as the ones detailed in U.S. Patent Application 20030171814 as incorporated by reference in the present application hereinabove. Specifically, the vertebral body replacements of U.S. patent application Ser. No. 10/403,598, published under no. 20030171814, analogous to the vertebral body replacements of the present application, can be inserted into intervertebral spaces through the use of grooves formed therein.

While certain, selected embodiments of the present invention have been disclosed herein, other embodiments of the apparatus and methods of the present invention will suggest themselves to persons skilled in the art in view of this disclosure. Therefore, it will be understood that variations and modifications can be effected within the spirit and scope of the invention and that the scope of the present invention should only be limited by the claims.

We claim:

1. A vertebral spacer comprising:
   a body having an upper surface and a lower surface, side surfaces defining a lateral width of the body, and an anterior face and a posterior face, wherein the anterior face and the posterior face extend from the lower surface to the upper surface, and wherein a maximum height of the anterior face is greater than a maximum height of the posterior face;
   a stabilizing body coupled against the posterior face of the body and having a lateral width greater than the lateral width of the body; and
   an attachment member coupling the body to the stabilizing body,
   wherein the posterior face of the body includes a first bore capable of receiving a portion of the attachment member, and
   wherein, when the body is coupled to the stabilizing body, a combination of the body and the stabilizing body defines a generally T-shaped configuration, when viewed from above the body upper surface or lower surface.

2. The vertebral spacer of claim 1, wherein the upper surface of the body is non-parallel to the lower surface of the body.

3. The vertebral spacer of claim 1, wherein the body has a rectangular cross-section as viewed along an axis extending perpendicular to the anterior face and to the posterior face.

4. The vertebral spacer of claim 1, wherein the body has an ellipsoidal cross-section.

5. The vertebral spacer of claim 1, wherein the attachment member has a shaft and a head, wherein the shaft of the attachment member has an anchoring region and a rotating region.

6. The vertebral spacer of claim 5, wherein the stabilizing body includes a second bore capable of receiving the rotating region of the shaft of the attachment member.

7. The vertebral spacer of claim 5, wherein the anchoring region of the shaft of the attachment member is secured to the first bore of the body by an adhesive, a threaded screw, a nut, a friction joint or a pin.

8. The vertebral spacer of claim 1, further comprising a locking assembly capable of interlocking the body with the stabilizing body.

9. The vertebral spacer of claim 8, wherein the locking assembly comprises a spring operated locking pin.

10. The vertebral spacer of claim 9, wherein the spring operated locking pin comprises a male member, a spring slideably disposed within a female member, and a second pin receiving bore.

11. The vertebral spacer of claim 10, wherein the spring operated locking assembly comprises a leaf spring having a locking arm, a communicating slot in the stabilizing body, and the attachment member has a receiving notch.

12. The vertebral spacer of claim 1, wherein the body has at least one protrusion capable of contacting a vertebra.

13. The vertebral spacer of claim 1, wherein the body has at least one protrusion on each of the upper surface and lower surface thereof.

14. The vertebral spacer of claim 1, wherein the body has a plurality of protrusions disposed thereon.

15. The vertebral spacer of claim 14, wherein the at least one protrusion has a cross-section selected from a triangle, a rectangle and a rounded form.

16. The vertebral spacer of claim 1, wherein the body has at least one liquid receiving bore and at least one traverse bore communicating with the at least one liquid receiving bore, and wherein the at least one traversing bore opens to the surface of the body.

17. The vertebral spacer of claim 16, wherein the stabilizing body is a hardened polymer extruded from the at least one traverse bore.

18. The vertebral spacer of claim 1, wherein the body further comprises at least one channel capable of receiving tissue growth.

19. The vertebral spacer of claim 18, wherein the channels have a tissue growth factor.

20. The vertebral spacer of claim 1, wherein the body is composed of a biocompatible material selected from the group consisting of a biocompatible polymer, a metal, bone or a combination thereof.

21. The vertebral spacer of claim 1, wherein the stabilizing body is composed of a material selected from the group consisting of a biocompatible polymer, a metal, bone or a combination thereof.

22. The vertebral spacer of claim 1, wherein the stabilizing body has a recess capable of accepting a posterior end of the body.

23. The vertebral spacer of claim 1 wherein the stabilizing body is releasably coupled to the body.

24. The vertebral spacer of claim 1, wherein the generally T-Shaped configuration is a first configuration of the vertebral spacer and wherein the body and the stabilizing body are rotatable relative to oneanother to occupy a second configuration in which the body and stabilizing body are rotated 90 degrees relative to oneanother as compared to the first configuration.

* * * * *